United States Patent [19]
Beldock et al.

[11] Patent Number: 5,621,013
[45] Date of Patent: Apr. 15, 1997

[54] INSECT REPELLENT BLENDS, LOTIONS, AND SPRAYS

[75] Inventors: Donald T. Beldock, Rye, N.Y.; John A. Beldock, Evergreen, Colo.; Grant Mudge, West Redding, Conn.

[73] Assignee: Primavera Laboratories, Inc., Rye, N.Y.

[21] Appl. No.: 520,101

[22] Filed: Aug. 28, 1995

Related U.S. Application Data

[60] Continuation-in-part of Ser. No. 298,839, Aug. 31, 1994, which is a division of Ser. No. 37,260, Mar. 26, 1993, Pat. No. 5,346,922, which is a division of Ser. No. 905,166, Jun. 24, 1992, Pat. No. 5,227,406.

[51] Int. Cl.⁶ ............................. A01N 31/02; A01N 31/04; A01N 31/06
[52] U.S. Cl. ..................... 514/703; 514/729; 514/739; 514/919; 424/195.1; 424/DIG. 10
[58] Field of Search ................... 514/703, 729, 514/739, 919; 424/195.1, DIG. 10

[56] References Cited

U.S. PATENT DOCUMENTS

| | | | |
|---|---|---|---|
| 3,988,432 | 10/1976 | Steltenkamp | 424/49 |
| 4,193,986 | 3/1980 | Cox | 424/28 |
| 4,478,853 | 10/1984 | Chaussee | 424/358 |
| 4,774,081 | 9/1988 | Flashinski et al. | 514/919 |
| 4,829,092 | 5/1989 | Nelson et al. | 514/738 |
| 5,227,406 | 7/1993 | Beldock et al. | 514/703 |
| 5,441,988 | 8/1995 | Butler et al. | 514/715 |

FOREIGN PATENT DOCUMENTS

| | | |
|---|---|---|
| 1230826 | 12/1987 | Canada . |
| 0275085 | 7/1988 | European Pat. Off. . |
| 855176 | 5/1940 | France . |
| 2622103 | 10/1987 | France . |
| 267202 | 3/1990 | Japan . |

OTHER PUBLICATIONS

Die Insektizide, Chemie, Wirkungsweise und Toxizitat, by Dr. Werner Perkow, 1968, pp. 533–540.
The Merck Index, Eleventh Edition, 1989, pp. 1072–1074.
Chemical Abstracts, vol. 112, 1990, p. 408, 164746e.
Chemicals Evaluated as Insecticides and Repellents at Orlando, FL, compiled by W. V. King, Agriculture Handbook, No. 69, May 1954.
Chemical Abstracts 104:30390K (1986).
Chemical Abstracts 113:110945W (1990).
Chemical Abstracts 105:204742Q (1986).
The Merck Index, 10th ed., Merck & Co., Inc., Rahway (NJ), 1983, pp. 332, 629, 1180–1181 and 1312.

*Primary Examiner*—John Pak
*Attorney, Agent, or Firm*—David P. Gordon

[57] ABSTRACT

Insect repellent blends, lotions, and sprays are provided. The insect repellent blend includes citronella, geraniol, crystalline 3,8 P-menthanediol (Chinese crystal), and terpineol and/or rhodinol. Preferably, the blend is dissolved or dispersed in a conveying medium so that the resulting product has weight percentages of approximately 0.05% citronella, approximately 0.06% geraniol, approximately 0.08 to 0.5% crystalline 3,8 P-menthanediol approximately 0.06% terpineol and/or approximately 0.08% rhodinol (extra). Four embodiments were tested against the efficacy of the individual ingredients and against an inert control. The interaction of ingredients in each of the embodiments was found by statistical analysis to be synergistic. The embodiments containing higher concentrations of the crystalline 3,8 P-menthanediol were found to have greater efficacy than the embodiments containing lower concentrations of crystalline 3,8 P-menthanediol. Little difference was observed between embodiments containing terpineol versus rhodinol extra.

19 Claims, 3 Drawing Sheets

INSECT REPLELLENT BLENDS, LOTIONS, AND SPRAYS

This application is a continuation-in-part of presently pending U.S. Ser. No. 08/298,839, filed on Aug. 31, 1994 which is a divisional of U.S. Ser. No. 08/037,260 filed on Mar. 26, 1993, now issued as U.S. Pat. No. 5,346,922, which in turn is a divisional of Serial No. 07/905,166 filed on Jun. 24, 1992, which is now issued as U.S. Pat. No. 5,227,406, the complete disclosures of which are hereby incorporated by reference herein.

BACKGROUND OF THE INVENTION

1. Field of the Invention

The present invention relates generally to insect repellents. More particularly, the present invention relates to synergistic blends of insect repellents, and to non-toxic lotions and sprays using the synergistic blends which may be used on humans and animals, where the repellents are particularly efficacious in repelling mosquitos.

2. State of the Art

In an attempt to repel insects, people have turned to widely marketed lotions and sprays (e.g. Cutters, Deep-Woods Off, and Tick Garde) which contain N,N-diethyl-m-toluamide (DEET) as their active ingredient. While DEET is an effective repellent, it is not particularly pleasing in smell, may sting when applied, and its use has a number of harmful side-effects to humans. DEET is injurious to eyes, mucous membranes, and sensitive skin. In addition, because DEET is absorbed through the skin, toxic systemic reactions may result as well. For example, in August 1989, the New York State Department of Health investigated five reports of generalized seizures which were believed to be associated with the topical application of DEET. Other symptoms and maladies associated with repeated exposure to DEET have included irritability, confusion, insomnia, encephalopathy, and coma. As a result, cautionary statements regarding use of DEET have been issued by the Centers for Disease Control and the states of New York, Connecticut, New Jersey, and Utah.

The potential hazards of using a product with DEET as an active ingredient suggests that there exists a great need for a comparably repellent product that is not dangerous to its users.

It is known that various herbal and floral extracts are useful in repelling insects. For example, citronella, is widely known as an insect repellent, although it is not nearly as effective as DEET.

The above-referenced U.S. Pat. Nos. 5,227,406 and 5,346,922 disclose a non-toxic, generally natural insect repellent product known as TREO® which includes terpineol ("T"), citronella ("C"), and one or both of rhodinol extra ("R") and geraniol ("G") as active ingredients provided in a conveying medium. The active ingredients are Used in small percentages, e.g. as little as 0.01%, preferably at between 0.05% and 0.08%, and preferably less than 1%, yet are synergistically efficacious, particularly against mosquitos and possibly against other insects such as Lyme-disease carrying ticks. The conveying medium can be a cosmetic moisturizer lotion, with or without a sun screen. For a spray, the conveying medium can be water or alcohol based. An attractive non-interfering fragrance is preferably provided as approximately 0.4% of the insect repellent product, and is capable of masking the fragrances of the actives because they are present in low concentrations. The lotion or spray is safely applied in liberal quantities to humans and animals without unpleasant side effects such as stinging. It was discovered in controlled studies that the combination of the terpineol, citronella, geraniol, and rhodinol extra ingredients is effective because of a synergistic interaction among the ingredients. It was also discovered that the sub-combination of the terpineol, citronella, and rhodinol extra ingredients, and the terpineol, citronella, and geraniol ingredients are also synergistic. Best results were obtained with TREO® having the following concentrations of ingredients: 0.06% terpineol, 0.05% citronella, 0.08% rhodinol extra, and 0.06% geraniol.

There have been reports in the literature that a plant derivative known as "Chinese crystal" is also an effective herbal insect repellent. Chinese crystal, a naturally occurring component of an essential oil obtained from China, is available from Shaw Mudge & Company, Stamford, Conn. under the name "Chinese Botanical I". It is a crystalline compound commonly referred to as 3,8 P Menthanediol (also known as 2-hydroxy a,a,4 trimethyl cyclohexane methanol and has a molecular structure as shown below in Diagram 1.

DIAGRAM 1

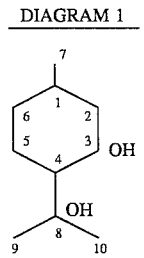

SUMMARY OF THE INVENTION

It is therefore an object of the invention to provide effective and safe insect repellent blends.

It is another object of the invention to provide effective insect repellent blends which are dispersed or dissolved in conveying media such as lotions, sprays, or the like.

It is a further object of the invention to provide an effective insect repellent which has an attractive fragrance.

It is an additional object of the invention to provide an effective insect repellent blend which can be used in conjunction with different conveying media.

It is also a further object of the invention to provide an insect repellent blend, spray, or lotion which effectively repels mosquitos, and other insects.

Another object of the invention is to provide a safe, effective insect repellent blend in a conveying medium which can be applied liberally to the face, skin, and clothing of a person.

It is yet another object of the invention to provide an insect repellent blend in a conveying medium which is safe and effective for animals.

An additional object of the invention is to provide an insect repellent blend in a conveying medium which utilizes generally safe herbal and floral extract ingredients or the natural oils that contain them, but which achieves an efficacy comparable to DEET.

A further object of the invention is to provide an insect repellent which may be impregnated into a fabric or plastic, incorporated into a sprayable mist, and be used in other applications such as surface treatments.

In accordance with the objects of the invention, an insect repellent blend is provided which includes Chinese crystal, citronella, geraniol, and one or both of terpineol and rhodinol (extra). The insect repellent blend preferably comprises from about 5% to about 25% by weight citronella, from about 5% to about 25% by weight geraniol, from about 30% to about 75% by weight Chinese crystal, and terpineol and/or rhodinol (extra) each being from about 5% to 30% by weight, such that the components of the blend total 100% by weight. The blend is typically dispersed or dissolved in a conveying medium such as a lotion, spray, or the like. When so dispersed or dissolved, the concentration of the components in the overall formulation generally ranges from about 0.01 to 1 weight percent geraniol, 0.01 to 1 weight percent citronella, 0.01 to 5 weight percent Chinese crystal, and terpineol and/or rhodinol in about 0.01 to 1 weight percent, with the balance comprising the conveying medium. The conveying medium may include moisturizers, sunscreen, fragrances, and other ingredients if desired.

An illustrative embodiment of the overall formation is an embodiment wherein the active insect repellent ingredients comprise about 0.06% terpineol, approximately 0.05% citronella, approximately 0.06% geraniol, approximately 0.5% Chinese crystal, and the balance comprising the conveying medium, wherein the percentages are by weight. In an alternative embodiment, the same ingredients are used, with the Chinese crystal being added in an amount of approximately 0.08%. In a further embodiment, the active insect repellent ingredients include by weight approximately 0.08% rhodinol extra, approximately 0.05% citronella, approximately 0.06% geraniol, and approximately 0.5% Chinese crystal, where the active ingredients are dissolved or dispersed in a conveying medium which comprises the balance. In still another embodiment, the active insect repellent ingredients include by weight approximately 0.08% rhodinol extra, approximately 0.05% citronella, approximately 0.06% geraniol, and approximately 0.08% Chinese crystal, where the active ingredients are dissolved or dispersed in a conveying medium which comprises the balance. The efficacy of several of the embodiments was tested against the efficacy of the individual ingredients and against a control. The interaction of ingredients in each of the embodiments tested was found by statistical analysis to be synergistic. The embodiments containing higher percentages of Chinese crystal were found to have greater efficacy than the embodiments containing lower percentages of Chinese crystal. Little difference was observed between embodiments containing terpineol versus rhodinol extra.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
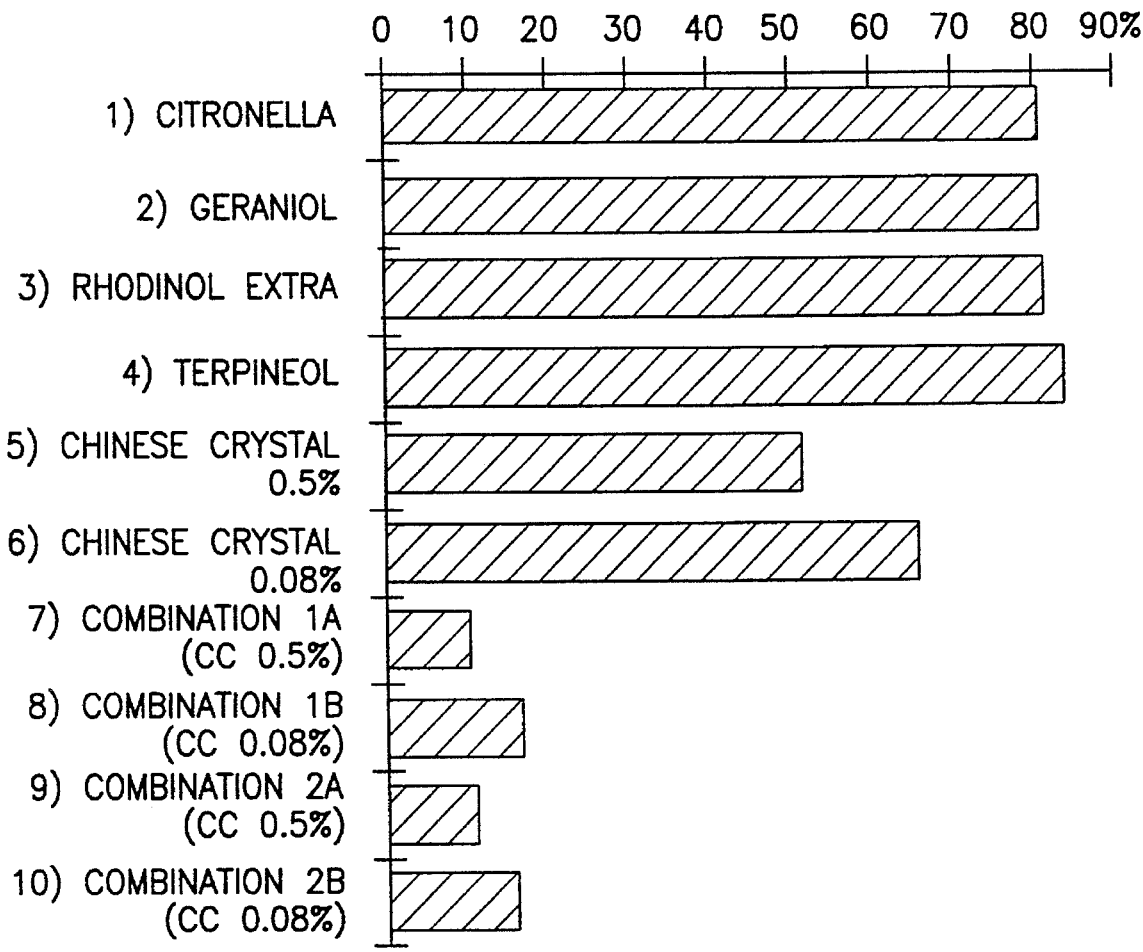
FIG. 1 is a bar graph showing mean repellency, as a percentage of biting rates observed in a control, for each of the embodiments of the invention tested and for each of the ingredients of the invention.

The insect repellent blend according to the invention includes a combination of Chinese crystal, citronella, geraniol, and either terpineol or rhodinol (extra). The blend is typically dispersed or dissolved in a conveying medium such as a lotion, spray, or the like. Four embodiments of the invention were tested as were the individual constituents of each embodiment and a control. Table 1 lists the various constituents (items 1–6) of the embodiments of the invention and their concentration as a weight percentage in a carrier of fragrance-free Lubrider™ skin Table 1 also lists the four embodiments of the invention (items 7–10) indicating the concentration of the active ingredients of each embodiment as a weight percentage in a carrier of fragrance-free Lubrider™ skin lotion. The first two embodiments, Combination 1A (item 7 in Table 1) and Combination 1B (item 8 in Table 1), have Chinese crystal, citronella, geraniol, and terpineol as ingredients and differ only in their concentration of Chinese crystal, 0.5% versus 0.08%. The second two embodiments, Combination 2A (item 9 in Table 1) and Combination 2B (item 10 in Table 1), have Chinese crystal, citronella, geraniol, and rhodinol extra as ingredients and differ only in their concentration of Chinese crystal, 0.5% versus 0.08%. Item 11 in Table 1, 100% fragrance-free Lubriderm™, was also tested as a control.

TABLE 1

List of Constituents, Combinations, and Control

| Constituent | Concentration (%) |
| --- | --- |
| 1) Citronella | 0.05 |
| 2) Geraniol | 0.06 |
| 3) Rhodinol Extra | 0.08 |
| 4) Terpineol | 0.06 |
| 5) Chinese Crystal | 0.08 |
| 6) Chinese Crystal | 0.5 |
| 7) Combination 1A: | |
| Chinese Crystal | 0.5 |
| Citronella | 0.05 |
| Geraniol | 0.06 |
| Terpineol | 0.06 |
| 8) Combination 1B: | |
| Chinese Crystal | 0.08 |
| Citronella | 0.05 |
| Geraniol | 0.06 |
| Terpineol | 0.06 |
| 9) Combination 2A: | |
| Chinese Crystal | 0.5 |
| Citronella | 0.05 |
| Geraniol | 0.06 |
| Rhodinol Extra | 0.08 |
| 10) Combination 2B: | |
| Chinese Crystal | 0.08 |
| Citronella | 0.05 |
| Geraniol | 0.06 |
| Rhodinol Extra | 0.08 |
| 11) Fragrance-free Lubriderm ™ Control | 100 |

Each of the constituents, combinations, and control in Table 1 was tested by treating a human hand with 1cc of the treatment and subjecting the treated hand to attack by Aedes aegypti mosquitos. The mosquitos were held in captivity in cubic Plexiglas™ cages (0.3 meters per side), with 200 mosquitos per cage, maintained on sugar water. Trials were conducted by placing the treated hand into a cage and counting the number of bites during a 15 second period. Testing was conducted for 110 trials for each the constituents, combinations, and control ("treatments"). Seven subjects participated in the testing. Hands were washed thoroughly with unscented soap between trials. The treatments were tested one after the other with the order randomized between trials. The number of bites on a control treated hand during a 15 second period varied from 5–33 over the 110 trials of the control, with a mean of 17.33, and a standard deviation of 6.65. Data from the 1,210 trials were pooled among subjects for analysis. The means and the 95% confidence intervals for each treatment were calculated. The 95% confidence interval is the range, estimated from the data, within which the next hypothetical data point collected from the same experiment would be expected to occur in 95% of the cases. Table 2 shows the calculated results for each treatment as a percentage of the biting rate of the control treatment. It will be understood that a lower percentage represents a higher repellency.

TABLE 2

Repellency Mean Values and 95% Confidence Intervals for Each Constituent and Combination Treatment Expressed as a Percentage of the Biting Rate of the Control Treatment

| Treatment | Lower 95% C.I. | Mean | Upper 95% C.I. |
|---|---|---|---|
| 1) Citronella .05% | 69.8 | 81 | 91.4 |
| 2) Geraniol .06% | 73 | 81.5 | 90 |
| 3) Rhodinol Extra .08% | 73 | 82 | 90 |
| 4) Terpineol .06% | 74 | 85 | 95 |
| 5) Chinese Crystal 0.5% | 45.4 | 52.6 | 59.8 |
| 6) Chinese Crystal 0.08% | 60 | 67.1 | 74.3 |
| 7) Combination 1A (CC 0.5%) | 9.2 | 11.3 | 13.4 |
| 8) Combination 1B (CC 0.08%) | 14.8 | 17.7 | 20.7 |
| 9) Combination 2A (CC 0.5%) | 10.3 | 13.1 | 15.8 |
| 10) Combination 2B (CC 0.08%) | 13.3 | 17.7 | 22.0 |

As shown in Table 2, the mean repellency rate of the citronella, geraniol, rhodinol extra, and terpineol when tested individually, varied from 81–85% of the biting rate of the control. Chinese Crystal (lines 6 and 7), exhibited a better repellency rate of about 52–67% of the biting rate of the control. Each of the combinations (lines 7–10) exhibited a dramatically better repellency rate than any of the ingredients, i.e. about 11–18% of the biting rate of the control.

The mean values shown in Table 2 are shown graphically in FIG. 1. Referring to Table 2 and FIG. 1, it can be seen that the most effective treatment was Combination 1A (line 7 of Table 2 and FIG. 1) which contained approximately 0.06% terpineol, approximately 0.05% citronella, approximately 0.06% geraniol, and approximately 0.5% Chinese crystal, exhibiting a mean repellency rate of 11.3%. Combination 2A (line 9 of Table 2 and FIG. 1) which contained approximately 0.08% rhodinol extra, approximately 0.05% citronella, approximately 0.06% geraniol, and approximately 0.5% Chinese crystal, was almost as effective, exhibiting a mean repellency rate of 13.1%. Combination 1B (line 8 of Table 2 and FIG. 1) which contained approximately 0.06% terpineol, approximately 0.05% citronella, approximately 0.06% geraniol, and approximately 0.08% Chinese crystal, and Combination 2B (line 10 of Table 2 and FIG. 1) which contained approximately 0.08% rhodinol extra, approximately 0.05% citronella, approximately 0.06% geraniol, and approximately 0.08% Chinese crystal, had the same mean repellency rate of 17.7%. These findings suggest that an increased concentration of Chinese crystal significantly increases repellency and that the contribution of rhodinol extra is substantially identical to the contribution of terpineol.

The analyzed data from the 1,210 trials were examined using the model of factorial additivity. Under this model, the mean and 95% confidence interval for each ingredient of each combination were combined multiplicatively. The resulting mean and "narrow sense additivity" predicts a mean and a confidence interval which would be expected of the combination if the contribution of each ingredient were simply "additive".

Figure 2:
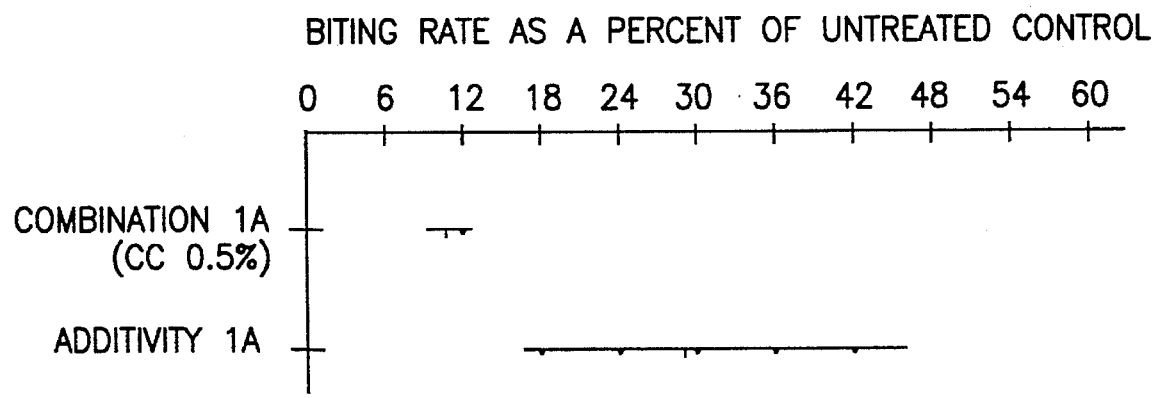
FIG. 2 is a graph of the 95% confidence intervals and the narrow sense additivity model for one embodiment of the invention.

The expected mean repellency of Combination 1A, therefore, is calculated by multiplying the observed mean repellency rates of each of the ingredients of Combination 1A. Referring to Table 2, it will be appreciated that the expected mean repellency of Combination 1A is 29.52%=(81% * 81.5% * 85% * 52.6%). Similarly, the expected 95% confidence interval (narrow sense additivity) for Combination 1A is 17.12% to 46.73%. It will be appreciated, however, that the observed mean repellency of Combination 1A was actually 11.3% which is much lower than the expected rate of 29.52%. In addition, the confidence interval of the observed treatment of Combination 1A (9.2% to 13.4%) is well below the expected confidence interval of 17.2% to 46.73%. The comparison of the observed mean and confidence interval for Combination 1A and the expected mean and narrow sense additivity is shown graphically in FIG. 2. The fact that there is no overlap between the confidence interval of Combination 1A and the narrow sense additivity model indicates that there is a statistically significant difference (of at least $P<0.05$) between the model and the data accumulated for Combination 1A. In other words, it is at least 95% probable that the interaction among the ingredients of Combination 1A is synergistic rather than merely additive.

Figure 3:
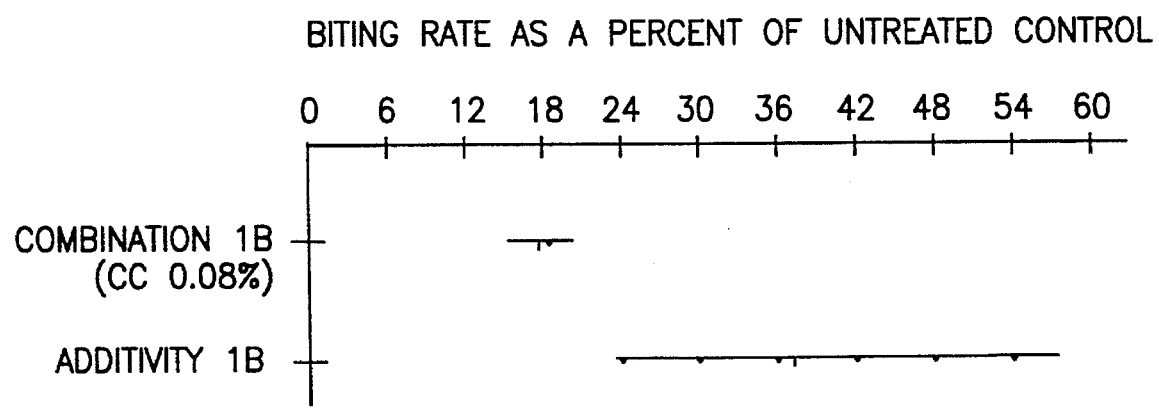
FIG. 3 is a graph of the 95% confidence intervals and the narrow sense additivity model for another embodiment of the invention.

The same analysis was applied to the data accumulated for Combination 1B and is represented graphically in FIG. 3. Referring to Table 2, it will be appreciated that the expected mean repellency of Combination 1B is 37.65%= (81% * 81.5% * 85% 67.1%). The expected 95% confidence interval (narrow sense additivity) for Combination 1B is 22.62% to 58.06%. It will be appreciated, however, that the observed mean repellency of Combination 1B was actually 17.7% which is much lower than the expected rate of 37.65%. In addition, the confidence interval of the observed treatment of Combination 1B (14.8% to 20.7%) is well below the expected confidence interval of 22.62% to 58.06% with no overlap. It is, therefore, at least 95% probable that the ingredients of Combination 1B act synergistically rather than additively.

Figure 4:
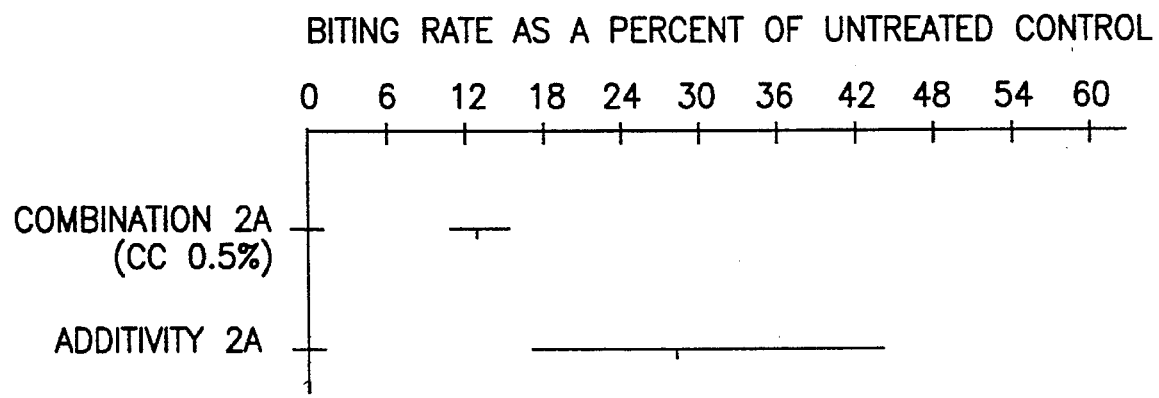
FIG. 4 is a graph of the 95% confidence intervals and the narrow sense additivity model for an additional embodiment of the invention.

Turning now to FIG. 4, and with reference to Table 2, the expected mean repellency of Combination 2A is 28.47%. The expected 95% confidence interval (narrow sense additivity) for Combination 2A is 18.69% to 44.27%. It will be appreciated, however, that the observed mean repellency of Combination 2A was actually 13.1% which is much lower than the expected rate of 28.47%. In addition, the confidence interval of the observed treatment of Combination 2A (10.3% to 15.8%) is well below the expected confidence interval of 18.69% to 44.27% with no overlap. It is, therefore, at least 95% probable that the ingredients of Combination 2A act synergistically rather than additively.

Figure 5:
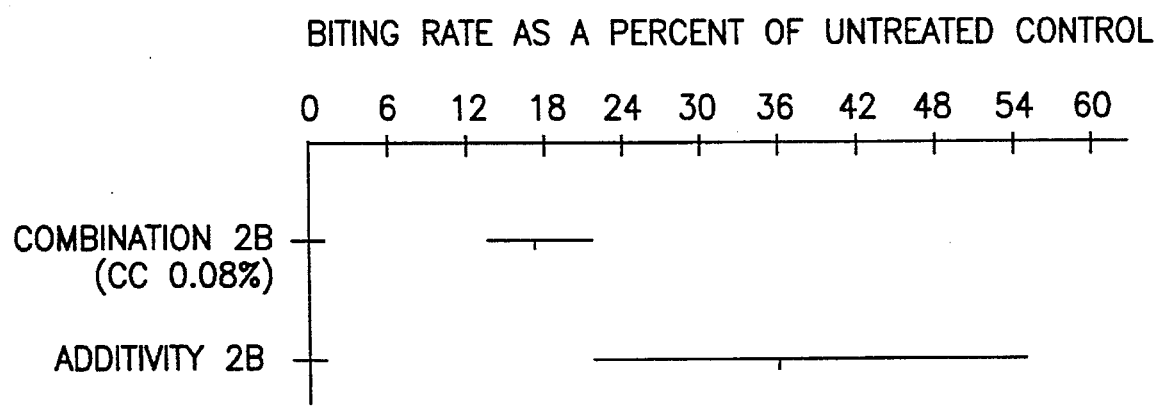
FIG. 5 is a graph of the 95% confidence intervals and the narrow sense additivity model for yet another embodiment of the invention.

The same analysis was applied to the data for Combination 2B and is demonstrated graphically in FIG. 5. The observed mean repellency of Combination 2B was actually 17.7% which is much lower than the expected rate of 36.32%. In addition, the confidence interval of the observed treatment of Combination 2B (13.3% to 22.0%) is below the expected confidence interval of 22.32% to 55.01% with no overlap. It is, therefore, at least 95% probable that the ingredients of Combination 2B act synergistically rather than additively.

Based on the above observations and analyses, it is concluded that each embodiment of the invention represents a synergistic interaction of ingredients. The mean repellency rates of each of the embodiments of the invention averaged two times better than what was predicted by the factorially additive model. In addition, the 95% confidence intervals predicted from the additivity models do not overlap those calculated for the observed performance of the embodiments of the invention. Thus, the actual performance of the embodiments of the invention is significantly superior to the performance predicted had there been no synergy among the ingredients. It is also worth noting that the performance of the embodiments of the invention was significantly less variable than the performance of the individual ingredients as indicated by the significantly narrower confidence intervals listed in Table 2. It is believed that the greater repellency of Combinations 1A and 2A as compared to Combinations 1B and 2B was due to the higher concentration of Chinese crystal, which was the most repellent of the individual constituents. It is also believed that the similar results obtained with Combinations 1A and 2A verses 1B and 2B was due to the similar repellency of terpineol and rhodinol extra. It is further believed that similar results are obtained when the active components of the insect repellent blend are employed with or without a conveying medium.

It is also noted that the tests reported herein were conducted using a species (Aedes aegypti) of mosquito which is widely maintained in laboratory colonies. This species is known to be more aggressive (less repelled) than other species. While no representations have been made regarding efficacy in the field, it is possible that even greater repellency may be observed with other species.

Further, it should be noted that the concentrations of citronella, geraniol, terpineol, and rhodinol extra used in the embodiments disclosed are the optimal concentrations of these ingredients disclosed in the above-referenced co-owned U.S. Pat. Nos. 5,227,406 and 5,346,922. It is therefore believed that the concentrations of these ingredients in the present invention would be subject to range limits similar to those of the above-referenced co-owned U.S. Pat. Nos. 5,227,406 and 5,346,922. In addition, it is believed that concentrations of Chinese crystal up to 5% in the overall formulation may be useful, as larger amounts of Chinese crystal are readily masked by non-interfering fragrances.

Further yet, it should be noted that while the described embodiments were described for use on human skin for effectively repelling mosquitos, the insect repellent is believed to repel other insects, and may be used on animals as well as humans.

Finally, it should be appreciated that while a preferred conveying medium for the insect repellent of the invention has been described, the conveying medium may take many forms. For example, the insect repellent of the invention may be incorporated into mediums including, but not limited to lotions, sprays, and creams. In fact, other active ingredients for other purposes, such as suntanning, sunscreening, sun-blocking, skin moisturizing, etc. can be added to the lotions, sprays or creams. Likewise, the insect repellent may be impregnated into a fabric or plastic in manners known in the art in which other repellents are impregnated into fabrics or plastics, thus effectively causing the fabric or plastic to become the conveying medium. Likewise, the insect repellent of the invention may be used in other applications such as surface treatments such as by incorporating the repellent into a wax or other surface coating.

There have been described herein synergistic insect repellent blends which incorporate Chinese crystal, citronella, geraniol, and either terpineol or rhodinol (extra), which can be dispersed or dissolved in a conveying medium such as a lotion or spray, such that the blend comprises a small percentage of the conveying medium. While particular embodiments have been described, it is not intended that the invention be limited thereto, as it is intended that the invention be as broad in scope as the art will allow. Thus, while preferred percentages and ranges of actives were described, it will be appreciated that different relative percentages of the active ingredients within those ranges could be utilized, although it is not known whether the resulting combination would be as efficacious as the preferred embodiments. Therefore, it will be appreciated by those skilled in the art that yet other modifications could be made to the provided invention without deviating from its spirit and scope as so claimed.

We claim:

1. An insect repellent, comprising:

a blend of geraniol, citronella, crystalline 3,8 P-menthanediol, and terpineol and/or rhodinol.

2. An insect repellent according to claim 1, wherein:

said geraniol comprises from about 5% to 25% by weight of said blend, said citronella comprises from about 5% to 25% by weight of said blend, said crystalline 3,8 P-menthanediol comprises from about 30% to 75% by weight of said blend, and said terpineol comprises from about 10% to about 30% by weight of said blend.

3. An insect repellent according to claim 1, wherein:

said geraniol comprises from about 5% to 25% by weight of said blend, said citronella comprises from about 5% to 25% by weight of said blend, said crystalline 3,8 P-menthanediol comprises from about 30% to 75% by weight of said blend, and said rhodinol comprises from about 10% to about 30% by weight of said blend.

4. An insect repellent according to claim 1, further comprising:

a conveying medium, wherein said blend is dispersed or dissolved in said conveying medium.

5. An insect repellent according to claim 4, wherein:

said geraniol constitutes at least 0.01% of the insect repellent, said citronella constitutes at least 0.01% of the insect repellent, and said crystalline 3,8 P-menthanediol constitutes at least 0.01% of the insect repellent, wherein all listed percentages (%) are weight percentages.

6. An insect repellent according to claim 5, wherein:

said geraniol constitutes no more than 1% of the insect repellent;

said citronella constitutes no more than 1% of the insect repellent; and said crystalline 3,8 P-menthanediol constitutes no more than 5% of the insect repellent, wherein all listed percentages (%) are weight percentages.

7. An insect repellent according to claim 4, wherein:

said geraniol constitutes about 0.01% to 1% by weight of said insect repellent, said citronella constitutes about 0.01% to 1% by weight of said insect repellent, said 3,8 P-menthanediol constitutes about 0.01% to 5% by weight of said insect repellent, said terpineol constitutes about 0.01% to 1% by weight of said insect repellent, said conveying comprises the balance of said insect repellent.

8. An insect repellent according to claim 7, wherein:

said 3,8 P-menthanediol constitutes approximately 0.08% by weight of said insect repellent.

9. An insect repellent according to claim 7, wherein:

said 3,8 P-menthanediol constitutes approximately 0.5% by weight of said insect repellent.

10. An insect repellent according to claim 8, wherein:

said geraniol constitutes approximately 0.06% by weight of said insect repellent, said citronella constitutes approximately 0.05% by weight of said insect repellent, and said terpineol constitutes approximately 0.06% by weight of said insect repellent.

11. An insect repellent according to claim 9, wherein:

said geraniol constitutes approximately 0.06% by weight of said insect repellent, said citronella constitutes approximately 0.05% by weight of said insect repellent, and said terpineol constitutes approximately 0.06% by weight of said insect repellent.

12. An insect repellent according to claim 4, wherein:

said geraniol constitutes about 0.01% to 1% by weight of said insect repellent, said citronella constitutes about 0.01% to 1% by weight of said insect repellent, said 3,8 P-menthanediol constitutes about 0.01% to 5% by weight of said insect repellent, said rhodinol constitutes about 0.01% to 1% by weight of said insect repellent, and said conveying comprises the balance of said insect repellent.

13. An insect repellent according to claim 12, wherein:

said 3,8 P-menthanediol constitutes approximately 0.08% by weight of said insect repellent.

14. An insect repellent according to claim 12, wherein:

said 3,8 P-menthanediol constitutes approximately 0.5% by weight of said insect repellent.

15. An insect repellent according to claim 13, wherein:

said geraniol constitutes approximately 0.06% by weight of said insect repellent, said citronella constitutes approximately 0.05% by weight of said insect repellent, and said rhodinol constitutes approximately 0.08% by weight of said insect repellent.

16. An insect repellent according to claim 14, wherein:

said geraniol constitutes approximately 0.06% by weight of said insect repellent, said citronella constitutes approximately 0.05% by weight of said insect repellent, and said rhodinol constitutes approximately 0.08% by weight of said insect repellent.

17. An insect repellent according to claim 12, wherein:

said terpineol constitutes about 0.01% to 1% by weight of said insect repellent.

18. An insect repellent according to claim 15, wherein:

said terpineol constitutes approximately 0.05% by weight of said insect repellent.

19. An insect repellent according to claim 16, wherein:

said terpineol constitutes approximately 0.05% by weight of said insect repellent.

* * * * *